United States Patent [19]

Brown et al.

[11] Patent Number: 4,534,965

[45] Date of Patent: Aug. 13, 1985

[54] CONTROLLING PLANT FUNGI USING STREPTOMYCETES GROWN ON CHITIN

[75] Inventors: Lewis R. Brown, Starkville; Susan Brown-Skrobot, Mississippi State, both of Miss.

[73] Assignee: Chevron Research Company, San Francisco, Calif.

[21] Appl. No.: 536,025

[22] Filed: Sep. 26, 1983

[51] Int. Cl.$^3$ .................. A01N 63/00; C12P 1/00; C12N 15/00; C12N 1/20; C12R 1/465; A01C 1/06; A01B 79/00

[52] U.S. Cl. .................................. 424/93; 435/253; 435/886; 435/172.1; 435/41; 47/57.6; 47/58

[58] Field of Search ................ 424/92, 93, 195; 435/911, 41, 172.1, 240, 886, 241, 243, 261, 253; 47/57.6, 58

[56] References Cited

U.S. PATENT DOCUMENTS 4,061,488 12/1977 Mann ............................. 71/77

OTHER PUBLICATIONS

De et al., *Current Science* p. 590 1978.
Hiragu et al., *Chemical Abst.* vol. 81 1974 p. 337 "Bacteriolytic Enzyme from Streptomyces".
*Chemical Abstracts* v. 97 1982 No. 51141g, Balasubramanya, R. H. et al., "Biological Control . . . Prawn--Shell Waste".
Putro, Sumpeno *Dissertation Abstracts* v. 43, No. 6, Dec. 1982 "Studies of the Suitability . . . Shrimp Waste . . .".
Price, J. S. et al., *J. of Bacteriology* v. 124 No. 3, Dec. 1975, "Production Purification, and Characterization of an Extracellular Chitosanase from Streptomyces".

*Primary Examiner*—Thomas G. Wiseman
*Assistant Examiner*—Robin Lyn Teskin
*Attorney, Agent, or Firm*—J. A. Buchanan, Jr.; T. G. DeJonghe

[57] ABSTRACT

A method and composition is provided to control fungal infection of seeds and seedlings. Certain species of Streptomyces are grown on dried ground shrimp waste preferably suspended in a mineral salts medium. The supernate derived from the culture provides fungal infection control when used as a seed-coating or seed-soaking material. The residue, consisting of unused shrimp waste and a Streptomyces species, also provides protection against fungal infection of plants such as cotton seedlings. The residue is employed as a amendment to the soil in the immediate area of the newly planted seed.

8 Claims, No Drawings

CONTROLLING PLANT FUNGI USING STREPTOMYCETES GROWN ON CHITIN

BACKGROUND OF THE INVENTION

The present invention relates to the control of fungal infection of plants using bacteria, in particular an actinomycete, that is antagonistic to, or produces a material(s) antagonistic to, the undesired fungi.

The loss of crops due to fungal infections is, in the aggregate, in the billions of dollars annually. Fungal infections can harm or destroy either the seed or the growing plant or both. To control or combat fungal infections a number of chemical compounds have been developed through extensive research. These chemical compounds are manufactured in chemical plants and then typically applied to the plants by spraying onto the plants in solution form.

The present invention is directed to a method of achieving fungal control by organisms and/or chemicals which are generated at the site of the plant—in the soil where the plant grows, using an actinomycete as a component to achieve the desired result.

Actinomycetes, such as organisms in the genus Streptomyces have been noted in the past as having antifungal effects. For example, Staib et al. in *Mycopathologia*, Vol. 70, 1:9-12, 1980 note that one strain of *Streptomyces griseus*, isolated from the roots of soil potted African violets, had an inhibitory effect against a number of fungi, including *Aspergillus niger*. De et al. in *Current Science*, p. 590, 1978 disclose the isolation of a soil streptomycete having broad antifungal activity against a number of fungi including phytopathogens and dermatophytes.

It also has been disclosed that the addition of chitin to soil results in an increase in the production of actinomycetes, Peterson et al. "The Influences of Chitin and Myxobacters on Numbers of Actinomycetes in Soil" *Canadian Journal of Microbiology*, Vol. 11, pp. 595-596, 1965. In some instances the chitin addition to soil has been reported as favorable toward control of plant diseases, but in the Peterson et al. report the chitin addition favored, rather than helped control, the spread of a Fusarium species of fungus.

Chitin is a white or colorless amorphous polysaccharide that forms part of the hard outer covering or internal layers of insects, crustaceans, and some other invertebrates.

SUMMARY OF THE INVENTION

According to the present invention, a method and composition are provided for controlling fungal infections of plants. The method comprises:

(a) growiing actinomycetes on a chitinous substrate in an aqueous medium for at least three days;
(b) separating an aqueous supernate from the solids preferably by centrifugation or decanting; and
(c) contacting unplanted seeds, from which the plants are to be grown, with the aqueous supernate.

In another embodiment of the present invention steps (a) and (b) are the same but for step (c), instead of contacting the seeds with supernate, the separated solids (unused chitin particles and streptomycete cells) are placed in the soil near the planted seeds or roots of the germinated plant.

According to still another embodiment of the present invention, both of these alternative last steps are practiced. That is, the unplanted seeds are contacted with the aqueous supernate and also after planting, or simultaneously with planting, the separated solids material is placed in the soil adjacent or near to the planted seeds or the germinated seeds.

It is believed that an antifungal substance(s) is produced while the actinomycetes grow on the chitin in aqueous slurry. This antifungal substance(s) appears to be present in both the aqueous supernate separated from the slurry and in the solids remaining after separating the supernate. Thus, either or both of these parts of the slurry can be used. The antifungal material may act like cycloheximide, which is an antifungal material produced by fermentation and used to control powdery mildew on roses and on rusts and leaf spots of lawn grasses.

Preferably the antinomycetes used in the method of the present invention are from the genus Streptomyces. The organisms in the genus Streptomyces are filamentous shaped bacteria in contrast to the more typical rod shaped bacteria, as in the genera Agrobacterium; Bacillus; Clostridium; Erwinia; Pseudomonas; and Xanthomonas.

The term "actinomycete" is used to embrace bacteria from the Actinomycetales order. The term "streptomycete" refers to bacteria from the Streptomyces genus. The Streptomyces genus is embraced within the Actinomycetales order, as set forth in Bergey's Manual, 8th Edition, Classification of Bacteria—1974.

We have found a particularly preferred Streptomyces species for use in the present invention, which species we identify herein as species No. 1. A culture deposit of this Streptomyces species No. 1 has been made at American Type Culture Collection, 1230 Parklawn Drive, Rockville, Md. 20852, and is identified by ATCC No. 39434.

We obtained the Streptomyces species No. 1 by isolation of the bacterium from a sample of Mississippi State soil.

Among other factors the present invention is based on our finding that particularly effective control of plant fungal infection is achieved using an actinomycete and chitin mixture, or supernate from such mixture, if the actinomycete is grown on the chitin prior to introduction of the actinomycete/chitin mixture to the soil or prior to coating or soaking of seed with supernate from the incubated solution of actinomycete/chitin. The growing time should be at least 3 days, preferably between 6 and 21 days. Also, an important aspect of the present invention is the continued generation of the actinomycete in the soil, that is in situ, for continued fungal control. Thus, in a preferred embodiment of the present invention the actinomycete and chitin are co-located in the soil with the roots of the plant so that the actinomycete will continue to grow and provide antifungal activity.

Shrimp waste is a particularly preferred source of chitinous material for the process of the present invention. Other sources of chitinous material include algae or fungi and various insects, such as roaches, ants and/or crickets.

Control of fungal infection of cotton plants, particularly *Rhizoctonia solani* control, is a preferred application for the method of the present invention. Other fungal diseases which can be controlled using the method of the present invention including diseases caused by organisms in the genera Alternaria, Cladosporium, Fusarium, Helminthesporium, Pestalotia, Phytophthora, Pythium, Rhizoctonia, Septoria, and Verticillium.

A preferred composition for fungal disease control, in accordance with the present invention, is Streptomyces species No. 1 grown on a chitinous substrate, especially a chitinous shrimp waste substrate. This composition is co-located near the seed or roots of a germinated seed as illustrated by examples below. The term "near" the plant or seed means at least within one foot of the plant or seed.

In brief, the composition used in the present invention may be obtained by adding a culture of streptomycete such as the preferred Streptomyces species No. 1 to a 1% by weight of dry ground shrimp waste in a mineral salts aqueous solution and allowing the streptomycete to grow for 3 to 15 days, preferably about seven days at about room temperature. Supernate material is taken off, for example, by centrifugation, and used to coat seeds. Thus, we have found that cotton seeds coated with or soaked in the supernate have a high resistance to fungal disease attack compared to cotton seeds which have not been so treated. The coating of the seeds may be by submersion in the aqueous supernate for a few seconds; preferably it is by soaking the seeds in the supernate for at least 2 minutes.

A preferred embodiment of the present invention is to use the shrimp waste and streptomycete cells separated by centrifuging the incubated mixture. In particular the separated solids material comprising shrimp waste and streptomycete cells is added as an amendment to the soil near the seeds or roots of the plants to thereby provide antifungal activity.

The amount of chitinous material such as shrimp waste added in the amendment to the soil near the location of the seed or roots of the plant preferably is at least 0.05 gram more preferably between 0.05 gram and 0.25 gram.

The number of streptomycete cells used in the soil amendment is important. A sufficient number of cells should be used so that the number of streptomycetes in the area near the seeds or plant roots is at least three times $10^5$ cells per gram of chitinous material, more preferably between about one times $10^6$ and one times $10^{10}$ cells per gram of chitinous amendment.

According to a preferred embodiment of the present invention, a method is provided for control of fungal diseases of plants which comprises placing in the soil near the seed of the plant, or near the roots of the germinated seed of the plant, a composition comprising chitinous material and Streptomyces species No. 1, wherein the streptomycete has been grown on chitinous material and the number of streptomycete cells is at least three times $10^5$ cells of Streptomyces per gram of chitinous material placed in the soil.

Although protection against fungal attack can be attained in accordance with the present invention by coating seeds with a supernate separated from a solution in which the streptomycete has been grown on a chitinous substrate, or protection can be achieved by adding to soil near the seeds or the roots of the plant an amendment comprising streptomycetes grown on the chitinous substrate, in accordance with a preferred embodiment of the present invention both of these are done to enhance control of fungal infection.

FURTHER DESCRIPTION AND EXAMPLES

EXAMPLES 1 AND 2

An inoculum of Streptomyces species No. 1 was grown on a shrimp waste (1%, w/v), mineral salts medium (1.0 g. $KNO_3$; 0.5 g. $K_2HPO_4.3H_2O$; 0.2 g. $MgSO_4.7H_2O$; 0.05 g. $FeCl_3.6H_2O$; 1.0 liter distilled $H_2O$) for seven days at room temperature (24° C.). The medium was sterilized at 121° C. for 15 minutes in an autoclave. Bottles containing 250 ml of the shrimp waste-mineral salts medium were inoculated with a 1 ml inoculum of Streptomyces species No. 1 and incubated for seven days at room temperature. The unused shrimp waste and streptomycete cells were removed by centrifugation, air dried, and saved for use later. Fifty ml of supernate were combined with 10 g of chitosan mixture (90 ml $H_2O$, 5 ml glacial acetic acid, 5 g chitosan) and employed as a seed coating for Stoneville 213, acid-delinted cotton seeds.

Seeds were dipped into the seed-coating material and air dried. All seeds (coated and uncoated) were planted 2 cm deep in styrofoam cups containing 50% BACC-TO ® Potting Mix and 50% garden soil inoculated with either 1% (w/w) R. solani or 10% (w/w) Pythium sp. When the streptomycete-shrimp waste amendment was employed, it was added to a hole punched in the potting mix-soil mixture prior to introduction of the seed. All cups were watered on a regular basis. Eighteen days after planting, plants and/or seeds were removed from the cups, examined microscopically for infection and cultured on Rose Bengal Agar. Samples of the soil were collected from the roots and/or area of the seed and subjected to analyses for numbers of streptomycetes and bacteria using Starch Casein Agar and Tryptic Soy Agar, respectively.

The results of the experiments as tabulated in Tables 1 and 2 below show that in the presence of the pathogenic fungi, all treatments receiving 50 or 100 mg of streptomycete-shrimp waste amendment produced a greater percentage of non-infected plants than did the controls which did not receive the amendment. Also, in general, the treated seeds (seeds dipped in supernate) produced greater numbers of non-infected plants than did the untreated seeds with amendment alone (averaging nearly 35% greater). The letters "CFU" in Tables 1 and 2 stand for colony-forming units.

TABLE 1

| | | The Effect of Seed Treatment and Soil Amendment on the Infection of Cotton by Pathogenic Fungi (Trial 1) using Streptomyces sp. No. 1 | | | | | |
|---|---|---|---|---|---|---|---|
| Pathogen | Seed* | mg. of Streptomycete-Shrimp Waste Amendment | Plants No. Germ. No. Planted | No. of Plants Infected | No. of Plants Not Infected | Streptomycetes No/g. of Soil | Bacteria CFU/g. Soil |
| None | U | 25 | 7/10 | 0 | 10 | $1.8 \times 10^7$ | $8.2 \times 10^7$ |
| None | U | 50 | 8/10 | 0 | 10 | $6.5 \times 10^7$ | $1.2 \times 10^7$ |
| None | U | 100 | 5/10 | 0 | 10 | $9.4 \times 10^8$ | $1.6 \times 10^6$ |
| None | T | 25 | 7/10 | 0 | 10 | $2.4 \times 10^7$ | $2.1 \times 10^7$ |
| None | T | 50 | 10/10 | 0 | 10 | $2.5 \times 10^8$ | $1.1 \times 10^7$ |
| None | T | 100 | 6/10 | 0 | 10 | $2.6 \times 10^8$ | $1.9 \times 10^6$ |

TABLE 1-continued

The Effect of Seed Treatment and Soil Amendment on the
Infection of Cotton by Pathogenic Fungi (Trial 1) using Streptomyces sp. No. 1

| Pathogen | Seed* | mg. of Streptomycete-Shrimp Waste Amendment | Plants No. Germ. No. Planted | No. of Plants Infected | No. of Plants Not Infected | Streptomycetes No/g. of Soil | Bacteria CFU/g. Soil |
|---|---|---|---|---|---|---|---|
| Pythium sp. | U | 0 | 6/10 | 3 | 3 | — | — |
| " | U | 25 | 8/10 | 6 | 2 | $4.3 \times 10^6$ | $7.3 \times 10^7$ |
| " | U | 50 | 10/10 | 7 | 3 | $2.9 \times 10^7$ | $8.1 \times 10^7$ |
| " | U | 100 | 9/10 | 5 | 4 | $3.3 \times 10^7$ | $1.2 \times 10^7$ |
| " | T | 25 | 9/10 | 5 | 4 | $7.2 \times 10^6$ | $5.9 \times 10^7$ |
| " | T | 50 | 8/10 | 1 | 7 | $2.1 \times 10^7$ | $8.4 \times 10^7$ |
| " | T | 100 | 10/10 | 2 | 8 | $4.8 \times 10^7$ | $1.1 \times 10^7$ |
| R. solani | U | 0 | 6/10 | 6 | 0 | — | — |
| " | U | 25 | 8/10 | 5 | 3 | $2.7 \times 10^6$ | $2.5 \times 10^7$ |
| " | U | 50 | 10/10 | 4 | 6 | $2.4 \times 10^7$ | $2.3 \times 10^7$ |
| " | U | 100 | 8/10 | 3 | 5 | $1.4 \times 10^7$ | $5.0 \times 10^8$ |
| " | T | 25 | 0/10 | 0 | 0 | $2.5 \times 10^4$ | $3.9 \times 10^8$ |
| " | T | 50 | 10/10 | 2 | 8 | $6.5 \times 10^6$ | $1.8 \times 10^7$ |
| " | T | 100 | 9/10 | 0 | 9 | $8.1 \times 10^7$ | $1.2 \times 10^7$ |

*U = Untreated; T = Treated

TABLE 2

The Effect of Seed Treatment and Soil Amendment on the
Infection of Cotton by Pathogenic Fungi (Trial 2) using Streptomyces sp. No. 1

| Pathogen | Seed* | mg. of Streptomycete-Shrimp Waste Amendment | Plants No. Germ. No. Planted | No. of Plants Infected | No. of Plants Not Infected | Streptomycetes No/g. of Soil | Bacteria CFU/g. Soil |
|---|---|---|---|---|---|---|---|
| None | U | 25 | 10/10 | 0 | 10 | $9.1 \times 10^6$ | $1.5 \times 10^7$ |
| None | U | 50 | 10/10 | 0 | 10 | $5.7 \times 10^6$ | $1.8 \times 10^7$ |
| None | U | 100 | 10/10 | 0 | 10 | $1.2 \times 10^6$ | $2.0 \times 10^6$ |
| None | T | 25 | 10/10 | 0 | 10 | $7.7 \times 10^6$ | $1.2 \times 10^7$ |
| None | T | 50 | 10/10 | 0 | 10 | $8.1 \times 10^6$ | $1.1 \times 10^7$ |
| None | T | 100 | 10/10 | 0 | 10 | $1.0 \times 10^8$ | $4.0 \times 10^6$ |
| Pythium sp. | U | 0 | 10/10 | 8 | 2 | $3.1 \times 10^4$ | $2.6 \times 10^6$ |
| " | T | 0 | 10/10 | 4 | 6 | $2.2 \times 10^5$ | $3.9 \times 10^6$ |
| " | U | 25 | 10/10 | 8 | 2 | $1.3 \times 10^5$ | $1.4 \times 10^7$ |
| " | U | 50 | 10/10 | 3 | 7 | $6.6 \times 10^7$ | $4.2 \times 10^6$ |
| " | U | 100 | 10/10 | 2 | 8 | $1.6 \times 10^8$ | $1.0 \times 10^7$ |
| " | T | 25 | 10/10 | 4 | 6 | $1.7 \times 10^7$ | $2.6 \times 10^7$ |
| " | T | 50 | 8/10 | 1 | 7 | $8.7 \times 10^7$ | $2.4 \times 10^7$ |
| " | T | 100 | 10/10 | 1 | 9 | $1.1 \times 10^8$ | $4.4 \times 10^6$ |
| R. Solani | U | 0 | 10/10 | 10 | 0 | $2.2 \times 10^4$ | $5.5 \times 10^6$ |
| " | T | 0 | 8/10 | 1 | 7 | $2.5 \times 10^5$ | $1.6 \times 10^6$ |
| " | U | 25 | 9/10 | 2 | 7 | $4.8 \times 10^6$ | $1.4 \times 10^7$ |
| " | U | 50 | 10/10 | 2 | 8 | $5.3 \times 10^6$ | $2.2 \times 10^7$ |
| " | U | 100 | 10/10 | 1 | 9 | $4.5 \times 10^7$ | $3.4 \times 10^6$ |
| " | T | 25 | 9/10 | 3 | 6 | $5.2 \times 10^6$ | $2.4 \times 10^7$ |
| " | T | 50 | 10/10 | 5 | 5 | $8.2 \times 10^6$ | $1.1 \times 10^7$ |
| " | T | 100 | 10/10 | 1 | 9 | $1.1 \times 10^7$ | $1.2 \times 10^7$ |

*U = Untreated; T = Treated

EXAMPLE 3

Table 3 below shows results for experiments in which three plant pathogenic fungi were employed. The pathogens and the amounts of inoculum added to the soil in the test cups were Pythium sp., 10% (w/w), Rhizoctonia sp., 1% (w/w), and Fusarium sp., 10% (w/w). Four different streptomycete cultures were employed and were designated Streptomyces sp. No. 1, Streptomyces sp. No. 2, Streptomyces sp. No. 3, and Streptomyces sp. No. 4. A different batch of Stoneville 213 delinted seeds were employed than those of Examples 1 and 2, and the substrate for planting consisted of 75% BACCTO ® Potting Soil and 25% soil from the Mississippi State University Experiment Station North Farm. No analyses for numbers of actinomycetes or bacteria were performed for this experiment.

The results (Table 3) obtained for Streptomyces sp. No. 1 were similar to those obtained in experiments covered by Tables 1 and 2. Also, of the four Streptomyces sp. tested, Streptomyces sp. No. 1 was the most effective in preventing fungal diseases while Streptomyces sp. No. 4 was the least effective. The use of Streptomyces sp. Nos. 1, 2, and 3 in combination did not perform better than Streptomyces sp. No. 1 alone.

TABLE 3

The Effect of Seed Treatment and Soil Amendment on the
Infection of Cotton by Pathogenic Fungi (Trial 3) using 4 different Streptomyces sp.

| Streptomyces sp. Used | Seed* | Streptomycete-Shrimp Waste Amendment (mg.) | Pathogen | Plants No. Germ. No. Plants | No. of Plants Infected | No. of Plants Not Infected |
|---|---|---|---|---|---|---|
| None | U | 0 | R. solani | 9/10 | 8 | 1 |
| 1 | U | 100 | " | 9/10 | 2 | 7 |
| 1 | T | 100 | " | 8/10 | 2 | 6 |
| 2 | U | 100 | " | 0/10 | — | — |
| 2 | T | 100 | " | 6/10 | 1 | 5 |
| 3 | U | 100 | " | 8/10 | 1 | 7 |
| 3 | T | 100 | " | 6/10 | 1 | 5 |
| 4 | U | 100 | " | 6/10 | 6 | 0 |
| 4 | T | 100 | " | 7/10 | 3 | 4 |
| 1,2,3 | U | 100 | " | 8/10 | 1 | 7 |
| 1,2,3 | T | 100 | " | 8/10 | 1 | 7 |
| None | U | 0 | Pythium sp. | 5/10 | 4 | 1 |
| 1 | U | 100 | " | 7/10 | 1 | 6 |
| 1 | T | 100 | " | 8/10 | 0 | 8 |
| 2 | U | 100 | " | 9/10 | 2 | 7 |
| 2 | T | 100 | " | 9/10 | 1 | 8 |
| 3 | U | 100 | " | 10/10 | 2 | 8 |
| 3 | T | 100 | " | 7/10 | 1 | 6 |
| 4 | U | 100 | " | 10/10 | 5 | 5 |
| 4 | T | 100 | " | 8/10 | 4 | 4 |
| 1,2,3 | U | 100 | " | 7/10 | 1 | 6 |
| 1,2,3 | T | 100 | " | 9/10 | 0 | 9 |
| None | U | 0 | Fusarium sp. | 0/10 | — | — |
| 1 | U | 100 | " | 8/10 | 1 | 7 |
| 1 | T | 100 | " | 10/10 | 2 | 8 |
| 2 | U | 100 | " | 10/10 | 2 | 8 |
| 2 | T | 100 | " | 10/10 | 3 | 7 |
| 3 | U | 100 | " | 7/10 | 2 | 5 |
| 3 | T | 100 | " | 7/10 | 4 | 3 |
| 4 | U | 100 | " | 7/10 | 5 | 2 |
| 4 | T | 100 | " | 10/10 | 5 | 5 |
| 1,2,3 | U | 100 | " | 10/10 | 3 | 7 |
| 1,2,3 | T | 100 | " | 5/10 | 1 | 4 |

*U = Untreated; T = Treated

EXAMPLE 4

Experiments were conducted to assess the effect of using streptomycete cells alone versus the use of shrimp waste containing the streptomycete, namely, Streptomyces sp. No. 1. The shrimp waste containing the Streptomyces sp. No. 1 and the general procedures used for the following tables, were as follows.

Sterile shrimp waste was prepared by subjecting dry ground shrimp waste to 121° C. for 15 minutes.

Treated shrimp waste was prepared by growing Streptomyces sp. No. 1 in mineral salts broth containing 1% (w/v) dried ground shrimp waste. After seven days of incubation under static conditions, the unused shrimp waste and streptomycete cells were separated by centrifugation and dried in an air oven at 45° C. to 50° C.

Sterile treated shrimp waste was prepared by growing Streptomyces sp. No. 1 in TSB (tryptic soy broth) containing 1% (w/w) dried shrimp waste for seven days, harvesting the unused shrimp waste by centrifugation, subjecting the treated shrimp waste to 65° C. to dry and sterilize the material. Although 65° C. will not normally sterilize, in the present case only the streptomycete is present and 65° C. is sufficient to destroy it. Thus, the material is sterile, i.e., devoid of all living matter.

In order to obtain treated shrimp waste containing various numbers of streptomycete cells, sterile treated shrimp waste was employed as a dry diluent to mix with the treated shrimp waste in a series of 1:10 dilutions.

Streptomyces sp. No. 1 was also grown in TSB for seven days, harvested by centrifugation, resuspended in sterile distilled water, and appropriate dilutions prepared in distilled water.

Potting mix was sterilized at 121° C. for 15 minutes and inoculated with 1% (w/w) Rhizoctonia solani.

The potting mix or soil-potting mix with placed in 4-oz. styrofoam cups. Two acid delinted Stoneville 213 cotton seeds were planted just beneath the surface of the potting mix or soil-potting mix. The appropriate amendments were added to the holes made in the potting mix or soil-potting mix prior to adding the seed.

Two separate batches of seeds were employed in the experiments and both batches demonstrated only slightly better than 50% germination in control tests.

The amendments employed were as follows.
(1) 0.1 g. sterile shrimp waste.
(2) 0.1 g. treated shrimp waste containing varying numbers of Streptomyces sp. No. 1
(3) 0.1 ml. of distilled water containing Streptomyces sp. No. 1 cells grown on TSB.
(4) 0.1 g sterile shrimp waste plus 0.1 ml. of distilled water containing Streptomyces sp. No. 1 cells grown on TSB.
(5) 0.1 g. sterile treated shrimp waste.
(6) 0.1 g. sterile treated shrimp waste plus 0.1 ml. of distilled water containing Streptomyces sp. No. 1 cells grown on TSB.

All seed containers were incubated under artificial light at room temperature. After germination and limited growth of the plants (14 days), each plant was examined for fungal infection.

Using the above procedures, in a first experimental set, $10^9$ cells of Streptomyces sp. No. 1 were employed in an amendment added to soil, and in a second set experiment $10^7$ cells were used. The combined data from these experimental sets are presented in Table 4. As can be observed, the streptomycetes alone were not nearly as effective in preventing infection of the seedlings as was the treated shrimp waste containing the added Streptomyces sp. No. 1 cells.

TABLE 4

The Control of *Rhizoctonia solani* Infection in Cotton Seedlings Using Cells of Streptomyces sp. No. 1 Grown on Tryptic Soy Broth

| Potting Material | Amendment | No. of Plants Infected | No. of Plants Not Infected | % Non-Infected Plants |
|---|---|---|---|---|
| p.m. | Streptomyces sp. No. 1 grown on TSB | 7 | 5 | 42 |
| p.m. + soil | Streptomyces sp. No. 1 grown on TSB | 7 | 8 | 53 |
| p.m. | Treated shrimp waste containing added Streptomyces sp. No. 1 | 6 | 23 | 79 |
| p.m. + soil | Treated shrimp waste containing added Streptomyces sp. No. 1 | 9 | 25 | 74 | p.m. = potting mix
TSB = Tryptic Soy Broth

EXAMPLE 5

Another set of experiments was conducted comparing results using an amendment of streptomycetes grown on a chitinous substrate versus use of streptomycetes grown on a non-chitinous substrate. The non-chitinous substrate is indicated in the table as TSB which is Tryptic Soy Broth. The results are shown in Table 5.

TABLE 5

The Control of *Rhizoctonia solani* Infection in Cotton Seedlings Using Mixtures of Shrimp Waste and Streptomyces sp. No. 1 Cells Grown on Tryptic Soy Broth

| Potting Material | Amendment | No. of Plants Infected | No. of Plants Not Infected | % Non-Infected Plants |
|---|---|---|---|---|
| p.m. | Sterile treated shrimp waste | 10 | 4 | 29 |
| Soil + p.m. | Sterile treated shrimp waste | 11 | 6 | 35 |
| p.m. | Sterile treated shrimp waste containing added Streptomyces sp. No. 1 grown on TSB | 4 | 10 | 71 |
| Soil + p.m. | Sterile treated shrimp waste containing added Streptomyces sp. No. 1 grown on TSB | 5 | 6 | 55 |
| p.m. | Shrimp waste containing added Streptomyces sp. No. 1 grown on TSB | 6 | 9 | 60 |
| Soil + p.m. | Shrimp waste containing added Streptomyces sp. No. 1 grown on TSB | 9 | 4 | 31 |
| p.m. | Treated shrimp waste containing added Streptomyces sp. No. 1 | 6 | 23 | 79 |
| Soil + p.m. | Treated shrimp waste containing added Streptomyces sp. No. 1 | 9 | 25 | 74 | p.m. = potting mix
TSB = Tryptic Soy Broth

EXAMPLE 6

Table 6 below presents data showing the effect of differing numbers of Streptomyces sp. No. 1 cells. Use of at least three times $10^4$ cells per 1/10 gram (which converts to three times $10^5$ cells per gram) of amendment was found to result in less than 56% of the cotton plants being infected with *R. solani* fungus. Use of seven times $10^6$ cells per gram of amendment was found to yield better control, with less than about 25% of the cotton plants showing signs of the fungal infection at such levels of use of Streptomyces sp. No. 1.

TABLE 6

The Control of *Rhizoctonia solani* Infection in Cotton Seedlings Using Treated Shrimp Waste Containing Different Numbers of Streptomyces sp. No. 1 Cells

| Potting Material | Amendment | No. of Plants Infected | No. of Plants Not Infected | % Non-Infected Plants |
|---|---|---|---|---|
| p.m. | Treated shrimp waste containing $7 \times 10^7$ Streptomyces sp. No. 1 cells | 6 | 21 | 78 |
| Soil + p.m. | Treated shrimp waste containing $7 \times 10^7$ Streptomyces sp. No. 1 cells | 4 | 12 | 75 |
| p.m. | Treated shrimp waste containing $7 \times 10^6$ Streptomyces sp. No. 1 cells | 4 | 16 | 80 |
| Soil + p.m. | Treated shrimp waste containing $7 \times 10^6$ Streptomyces sp. No. 1 cells | 4 | 12 | 75 |
| p.m. | Treated shrimp waste containing $3 \times 10^6$ Streptomyces sp. No. 1 cells | 2 | 7 | 78 |
| Soil + p.m. | Treated shrimp waste containing $3 \times 10^6$ Streptomyces sp. No. 1 cells | 5 | 13 | 72 |
| p.m. | Treated shrimp waste containing $7 \times 10^5$ Streptomyces sp. No. 1 cells | 1 | 8 | 89 |
| Soil + p.m. | Treated shrimp waste containing $7 \times 10^5$ Streptomyces sp. No. 1 cells | 1 | 3 | 75 |
| p.m. | Treated shrimp waste containing $3 \times 10^5$ Streptomyces sp. No. 1 cells | 3 | 8 | 73 |
| Soil + p.m. | Treated shrimp waste containing $3 \times 10^5$ Streptomyces sp. No. 1 cells | 4 | 8 | 67 |
| p.m. | Treated shrimp waste containing $7 \times 10^4$ Streptomyces sp. No. 1 cells | 4 | 11 | 73 |
| Soil + | Treated shrimp | 4 | 5 | 56 |

TABLE 6-continued

The Control of *Rhizoctonia solani* Infection in Cotton Seedlings Using Treated Shrimp Waste Containing Different Numbers of Streptomyces sp. No. 1 Cells

| Potting Material | Amendment | No. of Plants Infected | No. of Plants Not Infected | % Non-Infected Plants |
|---|---|---|---|---|
| p.m. | waste containing $7 \times 10^4$ Streptomyces sp. No. 1 cells | | | |
| p.m. | Treated shrimp waste containing $3 \times 10^4$ Streptomyces sp. No. 1 cells | 3 | 7 | 70 |
| Soil + p.m. | Treated shrimp waste containing $3 \times 10^4$ Streptomyces sp. No. 1 cells | 0 | 1 | 100 |
| p.m. | Treated shrimp waste containing $7 \times 10^3$ Streptomyces sp. No. 1 cells | 6 | 1 | 14 |
| Soil + p.m. | Treated shrimp waste containing $7 \times 10^3$ Streptomyces sp. No. 1 cells | 2 | 1 | 33 |
| p.m. | Treated shrimp waste containing $3 \times 10^3$ Streptomyces sp. No. 1 cells | 6 | 4 | 40 |
| Soil + p.m. | Treated shrimp waste containing $3 \times 10^3$ Streptomyces sp. No. 1 cells | 5 | 1 | 17 |
| p.m. | Treated shrimp waste containing $3 \times 10^2$ Streptomyces sp. No. 1 cells | 5 | 2 | 29 |
| Soil + p.m. | Treated shrimp waste containing $3 \times 10^2$ Streptomyces sp. No. 1 cells | 2 | 0 | 0 | p.m. = potting mix

What is claimed is:

1. A biologically pure culture of species No. 1 which has been deposited under ATCC 39434.

2. A phytopathogenic fungi controlling composition which comprises a fungicidally effective amount of (1) Streptomyces species No. 1 which has been deposited under ATCC 39434; and (2) a chitinous substrate.

3. A phytopathogenic fungi controlling composition in accordance with claim 1 wherein the chitinous substrate is shrimp waste.

4. A method for controlling phytopathogenic fungi on plants which comprises placing in the soil near the seed of the plant or the roots of the germinated seed of the plant a phytopathogenic fungi controlling composition containing a fungicidally effective amount of (1) Streptomyces species No. 1 which has been deposited under ATCC 39434; and (2) a chitinous substrate.

5. A method in accordance with claim 4 wherein the chitinous substrate is selected from the group consisting of shrimp waste chitin, insect chitin, algal chitin and fungal chitin.

6. A method in accordance with claim 5 wherein the chitinous substrate is shrimp waste.

7. A method in accordance with claim 4 wherein the plants are cotton plants.

8. A method in accordance with claim 7 wherein the phytopathogenic fungi are *Rhizoctania solani*.

* * * * *